US012779122B2

(12) United States Patent
O'Hare et al.

(10) Patent No.: US 12,779,122 B2
(45) Date of Patent: Nov. 3, 2026

(54) WIRELESS DATA COMMUNICATION ACCESSORY FOR A DRUG DELIVERY DEVICE

(71) Applicant: Sanofi, Paris (FR)

(72) Inventors: Aidan Michael O'Hare, Warwick (GB); Oliver Charles Gazeley, Warwick (GB); Stefan Alt, Frankfurt am Main (DE)

(73) Assignee: Sanofi, Paris (FR)

( * ) Notice: Subject to any disclaimer, the term of this patent is extended or adjusted under 35 U.S.C. 154(b) by 1132 days.

(21) Appl. No.: 17/776,553

(22) PCT Filed: Nov. 11, 2020

(86) PCT No.: PCT/EP2020/081785
§ 371 (c)(1),
(2) Date: May 12, 2022

(87) PCT Pub. No.: WO2021/094388
PCT Pub. Date: May 20, 2021

(65) Prior Publication Data

US 2022/0395641 A1 Dec. 15, 2022

(30) Foreign Application Priority Data

Nov. 14, 2019 (EP) .................................... 19306467

(51) Int. Cl.
*A61M 5/20* (2006.01)
*H04B 5/26* (2024.01)
(Continued)

(52) U.S. Cl.
CPC ................. *A61M 5/20* (2013.01); *H04B 5/26* (2024.01); *H04B 5/266* (2024.01); *H04W 4/023* (2013.01);
(Continued)

(58) Field of Classification Search
CPC .......... A61M 5/003; A61M 2005/2006; A61M 2205/3584; A61M 5/20;
(Continued)

(56) References Cited

U.S. PATENT DOCUMENTS 10,997,544 B1 * 5/2021 Bar-Zeev ................. B64F 1/18
2008/0167615 A1 7/2008 Niehoff
(Continued)

FOREIGN PATENT DOCUMENTS

CN 104081431 A 10/2014
CN 107029319 A 8/2017
(Continued)

OTHER PUBLICATIONS

International Preliminary Report on Patentability in International Appln. No. PCT/EP2020/081785, mailed on May 27, 2022, 9 pages.
(Continued)

*Primary Examiner* — Cindy Trandai
(74) *Attorney, Agent, or Firm* — Fish & Richardson P.C.

(57) ABSTRACT

A wireless data communication accessory is disclosed, which is configured for attachment to a drug delivery device and comprises an interface for data exchange between the accessory and the drug delivery device, wireless communication means configured to communicate with an external device paired with the wireless communication means via wireless communication, and a controller coupled to the interface and the wireless communication means and being configured to control operation of the interface and the wireless communication means such that data received from the drug delivery device via the interface are processed for transmission to the external device via the wireless communication.

9 Claims, 7 Drawing Sheets

(51) Int. Cl.
*H04W 4/02* (2018.01)
*H04W 4/80* (2018.01)

(52) U.S. Cl.
CPC ...... *H04W 4/80* (2018.02); *A61M 2005/2006* (2013.01); *A61M 2205/3334* (2013.01); *A61M 2205/3561* (2013.01); *A61M 2205/3584* (2013.01); *A61M 2205/3592* (2013.01); *A61M 2205/50* (2013.01); *A61M 2205/8212* (2013.01)

(58) Field of Classification Search
CPC .. A61M 2205/3334; A61M 2205/3561; A61B 5/0004; A61B 5/4839; A61B 5/746; H04B 5/26; H04B 5/266; H04W 4/023; H04W 4/80
See application file for complete search history.

(56) References Cited

U.S. PATENT DOCUMENTS

| | | | | |
|---|---|---|---|---|
| 2011/0295215 | A1* | 12/2011 | Nielsen | G16H 20/17 604/257 |
| 2011/0313395 | A1* | 12/2011 | Krulevitch | A61M 5/31525 604/82 |
| 2013/0117696 | A1 | 5/2013 | Robertson et al. | |
| 2013/0178826 | A1* | 7/2013 | Li | A61M 5/155 604/145 |
| 2013/0245545 | A1* | 9/2013 | Arnold | A61M 5/1723 604/66 |
| 2014/0330243 | A1 | 11/2014 | Kietzmann et al. | |
| 2017/0006414 | A1* | 1/2017 | Tomassini | H04W 4/80 |
| 2018/0154086 | A1 | 6/2018 | Toporek et al. | |
| 2019/0134305 | A1 | 5/2019 | Srinivasan et al. | |
| 2019/0184093 | A1* | 6/2019 | Sjolund | A61B 5/14532 |
| 2019/0201627 | A1 | 7/2019 | Helmer et al. | |
| 2020/0280844 | A1* | 9/2020 | Mizota | H04W 12/63 |
| 2021/0209433 | A1* | 7/2021 | Welle | G01F 23/296 |
| 2021/0330891 | A1* | 10/2021 | Byerly | A61M 5/31551 |

FOREIGN PATENT DOCUMENTS

| | | | |
|---|---|---|---|
| CN | 109641103 | A | 4/2019 |
| EP | 3476417 | | 5/2019 |
| JP | 2013-116402 | A | 6/2013 |
| JP | 2018-506401 | A | 3/2018 |
| JP | 2018-508275 | A | 3/2018 |
| JP | 2018-517502 | A | 7/2018 |
| WO | WO 2014/152704 | | 9/2014 |
| WO | WO 2016/110592 | | 7/2016 |
| WO | WO 2016/120207 | A1 | 8/2016 |
| WO | WO 2016/128207 | A1 | 8/2016 |
| WO | WO 2016/198516 | A1 | 12/2016 |
| WO | WO 2018/041798 | A1 | 3/2018 |
| WO | WO 2018/104422 | | 6/2018 |

OTHER PUBLICATIONS

International Search Report and Written Opinion in International Appln. No. PCT/EP2020/081785, mailed on Jan. 25, 2021, 11 pages.

* cited by examiner

WIRELESS DATA COMMUNICATION ACCESSORY FOR A DRUG DELIVERY DEVICE

CROSS REFERENCE TO RELATED APPLICATIONS

The present application is the national stage entry of International Patent Application No. PCT/EP2020/081785, filed on Nov. 11, 2020, and claims priority to Application No. EP 19306467.2, filed on Nov. 14, 2019, the disclosures of which are incorporated herein by reference.

TECHNICAL FIELD

The present disclosure relates to a wireless data communication accessory for a drug delivery device, particularly a drug injection device.

BACKGROUND

A variety of diseases exists that require regular treatment by delivery, particularly injection of a medicament. Such injection can be performed by using injection devices, which are applied either by medical personnel or by patients themselves.

Drug injection devices particularly for usage by patients themselves may be equipped with electronics for measuring and storing data related to the usage. The usage related data may also be transmitted via a wireless link or a wireline connection to an external device such as a smartphone, a tablet or laptop computer, or in the cloud. For example, US 2019/0134305 A1 discloses a medication delivery device, for example an injection pen or a wearable pump, which can be paired with an external device for providing data captured from a flow sensor relating to medicine delivery to a patient to a paired external device. The device can have Bluetooth® communication and/or near field communication (NFC) circuits for proximity-based pairing and connectivity with the external device for real-time or deferred transfer of captured data to the external device.

EP 3 476 417 A1 relates to drug delivery systems for delivering, administering, injecting, infusing and/or dispensing liquids including a drug, medicament, or active ingredient. WO2016/110592A1 relates to a wireless data communication module fora drug injection device. WO2014/152704A1 relates generally to a smart insulin or medicament delivery device that records, for example, the flow, dose of an insulin or medicament injection and/or other medicament-related parameter or fluid-type medicament delivery parameter, and communicates wirelessly with a portable system and controller.

SUMMARY

In one aspect the present disclosure provides a wireless data communication accessory configured for attachment to a drug delivery device comprising an interface for data exchange between the accessory and the drug delivery device, wireless communication means configured to communicate with an external device paired with the wireless communication means via wireless communication, and a controller coupled to the interface and the wireless communication means and being configured to control operation of the interface and the wireless communication means such that data received from the drug delivery device via the interface are processed for transmission to the external device via the wireless communication.

In embodiments, the interface may comprise wired communication means comprising at least one contact for electrically connecting to at least one contact of the drug delivery device when the accessory being attached to the drug delivery device and interface circuitry configured for data exchange via the at least one contact.

The accessory allows to add wireless communication functionality to a drug delivery device without modifying the device itself. The controller of the accessory may be regarded as a communication protocol converter, which convert a data protocol of the interface for data exchange between the accessory and the drug delivery device to a data protocol for communication between the wireless communication means and the external device. The interface for data exchange between the accessory and the drug delivery device may comprise a wired and/or wireless interface, allowing a flexible use of the accessory with drug injection devices having different data exchange interfaces. The wired communication means enable a data exchange between the drug delivery device and the accessory with a very low power consumption, and, thus, for example allow extending life of a battery of the accessory supplying power for the data exchange. Also, the technical complexity of a wired communication is usually lower than for a wireless communication. The accessory allows upgrading the functionality of a drug delivery device. Thus, the technical complexity of drug injection devices can be reduced due to the accessory, which may comprise functionality usable with different drug delivery devices and, thus, may be reusable, while a drug delivery device may be dispensable.

In embodiments, the interface may comprise second wireless communication means configured for generating a radio frequency field for powering passive short-range wireless communication means of the drug delivery device and receiving data from the passive short-range wireless communication means via short-range communication. For example, a drug delivery device may merely comprise a small battery for powering drug usage detection electronics contained in the device or even no battery at all besides the passive short-range wireless communication means, which are powered by the radio frequency field of the second wireless communication means comprised by the accessory, which may contain a larger battery configured to supply the second wireless communication means as well as the controller and the wireless communication means. Thus, the term "second wireless communication means" designates wireless communication means requiring a power supply such as a battery to actively communicate over short ranges typically in the order of centimetres. The term "passive short-range wireless communication means" designates wireless communication means, which can be powered by the energy taken from a received radio frequency field in their close proximity and to communicate over short ranges typically in the order of centimetres.

In more specific embodiments, the second wireless communication means may be configured for generating the radio frequency field within a proximity on the order of centimetres and the wireless communication means are configured to communicate with the paired external device within a proximity on the order of meters. Due to the required relatively small radio frequency field extension generated by the second wireless communication means, the energy consumption may be reduced. Thus, if the accessory contains a battery as power supply, the battery lifetime may be increased.

In more specific embodiments, the second wireless communication means may comprise NFC reader circuitry with an antenna configured for NFC communication and/or the wireless communication means may comprise a Bluetooth® communication circuitry with an antenna configured for Bluetooth® communication. This allows to implement technically less complex passive NFC communication means in the drug delivery device. The Bluetooth® technology allows a reliable communication over larger distances compared to NFC, which can also be implemented with low energy requirements according to the Bluetooth® LE standard. For example, the accessory may be attached to the drug delivery device such that a NFC communication can be established between the device and the accessory for data exchange, particularly for reading data by the accessory from the device, and the data received by the accessory from the device can be transmitted via a Bluetooth® connection to an external device, e.g. a smartphone, a tablet computer, a laptop computer, a desktop computer.

In more specific embodiments, the interface circuitry may comprise a serial communications interface circuitry, particularly an UART interface, an I2C bus interface, a Serial Peripheral Interface, or a 1-wire interface. A serial communication link has the advantage of a limited number of lines, and, thus, allows to reduce the implementation effort. Also, the number of contacts is smaller than for example as required for a parallel communication link, allowing to reduce the efforts for implementing the interface.

In more specific embodiments, the at least one contact of the wired communication means may comprise one or more sprung contacts. A sprung contact may increase the reliability of an electrical connection between to connected contacts.

In more specific embodiments, the wired communication means may be configured to source an electric current via the at least one contact, wherein the electric current may be generated to source an electric current in one or more contacts of an antenna of the drug delivery device such that the wired communication means can read a signal modulation by the drug delivery device on the antenna. For example, the wired communication means may comprise wireless signal generation circuitry, but not an antenna, but instead provide the generated wireless signal as electric current via the at least one contact. The at least one contact then source the electric current in one or more contacts of the antenna of the drug delivery device, wherein the sourced electric current corresponds to an electric current sourced by a radio frequency field. An advantage of this kind of communication may be seen in the lower signal level of the sourced electric current in contrast to a signal transmission via a radio frequency field, and in the potentially a lower power consumption for data exchange. Another advantage might be seen in the potential for reducing the overall amount of electrical components.

In more specific embodiments, the wired communication means may comprise a NFC reader circuitry being configured to implement a physical layer of a communications protocol layer being adapted for generating the electric current to source the electric current in one or more contacts of an antenna of the drug delivery device such that the wired communication means can read a signal modulation by the drug delivery device on the antenna.

In embodiments, the accessory may comprise a housing being cap-like shaped for pinning on one end of a pen-like shaped drug delivery device. The accessory can then be clipped on the one end of the pen-liked shaped drug delivery device, particularly making assembly of the drug delivery device and the accessory easy to handle for users.

In more specific embodiments, at least one antenna may be provided at one or more locations of the housing such that the at least one antenna is inductively coupled to an antenna of passive short-range wireless communication means of the drug delivery device when the accessory is attached to the one end of the drug delivery device. For example, when the accessory is fully attached to the drug delivery device, an antenna provided at a specific location of the housing may be located vis-à-vis an antenna provided at a body of the drug delivery device so that a wireless link can established with a minimum of performance loss.

In more specific embodiments, one of the at least one antenna may be provided in a protruding part of the housing, which overlaps the one end of the drug delivery device when the accessory is attached to the one end of the drug delivery device. This embodiment is particularly suitable for a drug delivery device with an antenna located parallel to the axis of the device.

In more specific embodiments, one of the at least one antenna may be provided in a cover part of the housing, which lies opposite to the one end of the drug delivery device when the accessory is attached to the one end of the drug delivery device. This embodiment is particularly provided for a drug delivery device with an antenna located in one end of its body. The accessory may for example be pinned on a knob provided for dosage selection and delivery.

In other embodiments, the accessory may comprise a housing being sleeve-like shaped for pinning on a body of a pen-like shaped drug delivery device. In this embodiment, each end of the body of the drug delivery device is not covered by the accessory, and for example a dosage selection and delivery knob provided at one of the ends of the body is freely accessible by a user.

In more specific embodiments, at least one antenna may be provided at one or more locations of the housing such that the at least one antenna is inductively coupled to an antenna of passive short-range wireless communication means of the drug delivery device when the accessory is attached to the body of the drug delivery device. For example, an antenna may be provided at a middle section of the housing, and the sleeve-like shaped accessory may be slipped over the body and located over the middle section with the antenna so that both antennas are closely located to each other and data exchange via wireless link can be accomplished with minimum loss.

In embodiments, the housing may comprise at least at the one or more locations of the housing, at which the at least one antenna is provided, a passive absorbing shielding and/or an active suppressive shielding for shielding the at least one antenna from the outside of the accessory. The shielding may suppress radio frequency radiation external to the drug delivery device and accessory from influencing data exchange of a wired or wireless link between the accessory and drug delivery device. Also, radio frequency radiation of a wireless link between the accessory and drug delivery device is blocked by the shielding so that interception of the data exchange is prevented.

In embodiments, the accessory may further comprise detection means configured to detect a usage of the drug delivery device and to activate a power supply of the accessory upon a detected usage when the accessory being attached to the drug delivery device. The detection means may comprise for example by a mechanical, magnetic or capacitive switch, which may be activated for example by applying a force on the mechanical switch, by altering a magnetic field acting on the magnetic switch, or by touching a sensitive portion of the capacitive switch.

In more specific embodiments, the detection means may be configured to detect a dosage selection on and/or a dosage delivery by the drug delivery device as a usage of the drug delivery device. The detection means may for example comprise a magnetic switch located near a dosage selection and delivery mechanism of the drug delivery device when the accessory is attached to the device. When a user selects a dosage and/or presses a knob to deliver a dosage, a magnet may be moved by the mechanism activating the magnetic switch to close and to activate the power supply of the accessory. In that way, the accessory may be powered on without any specific interaction of the user making usage of the accessory and drug delivery device more comfortable.

In another aspect, the present disclosure provides a drug delivery device comprising

- a body for holding a drug container,
- a dosage selection mechanism for selecting a drug dosage to be delivered, and an interface for data exchange between the drug delivery device and an accessory as disclosed herein and being attached to the drug delivery device. The data exchange may comprise data related to the drug delivery device, particularly the drug contained in the device, dose related data such as for example selected and expelled dosages and further device related data, for example drug delivery device configuration data such as time and date of first usage, last usage, number of usages, etc.

In embodiments, the drug delivery device may comprise a controller coupled to the dosage selection mechanism and the interface and being configured to control operation of the interface such that data related to a selected and delivered drug dosage received from the dosage selection mechanism are processed for transmission to the attached accessory via the interface. The drug delivery device may be for example an injection pen comprising a pen-like shaped body holding a drug cartridge and comprising a syringe on one end and the dosage selection mechanism on the other end. The dosage selection mechanism may comprise a button to be pressed for delivery of a selected dosage. The interface and controller be contained in the dosage button together with a battery for powering at least the controller upon a dosage selection.

In embodiments, the interface may comprise at least one of the following: passive short-range wireless communication means;

wired communication means comprising at least one contact for electrically connecting to at least one contact of the accessory when the accessory being attached to the drug delivery device and interface circuitry configured for data exchange via the at least one contact.

In more specific embodiments, the passive short-range wireless communication means may be configured for being powered by a radio frequency field generated within a proximity on the order of centimetres. This allows to employ a smaller battery in the drug delivery device and to safe space required for the battery in the device.

In more specific embodiments, the interface circuitry of the wired communication means may comprise a serial communications interface circuitry, particularly an UART interface, an I2C bus interface, a Serial Peripheral Interface, or a 1-wire interface.

In more specific embodiments, the at least one contact of the wired communication means may comprise one or more conductive pads. The one or more conductive pads may be for example located at one end of an elongated body of the drug delivery device on which the accessory can be attached.

In more specific embodiments, the one or more conductive pads may be connections of an antenna of the passive short-range wireless communication means.

DETAILED DESCRIPTION

In the following, embodiments of the present disclosure will be described with reference to injection devices, particularly an injection device in the form of a pen. The present disclosure is however not limited to such application and may equally well be deployed with other types of drug delivery devices, particularly with another shape than a pen.

Figure 1:
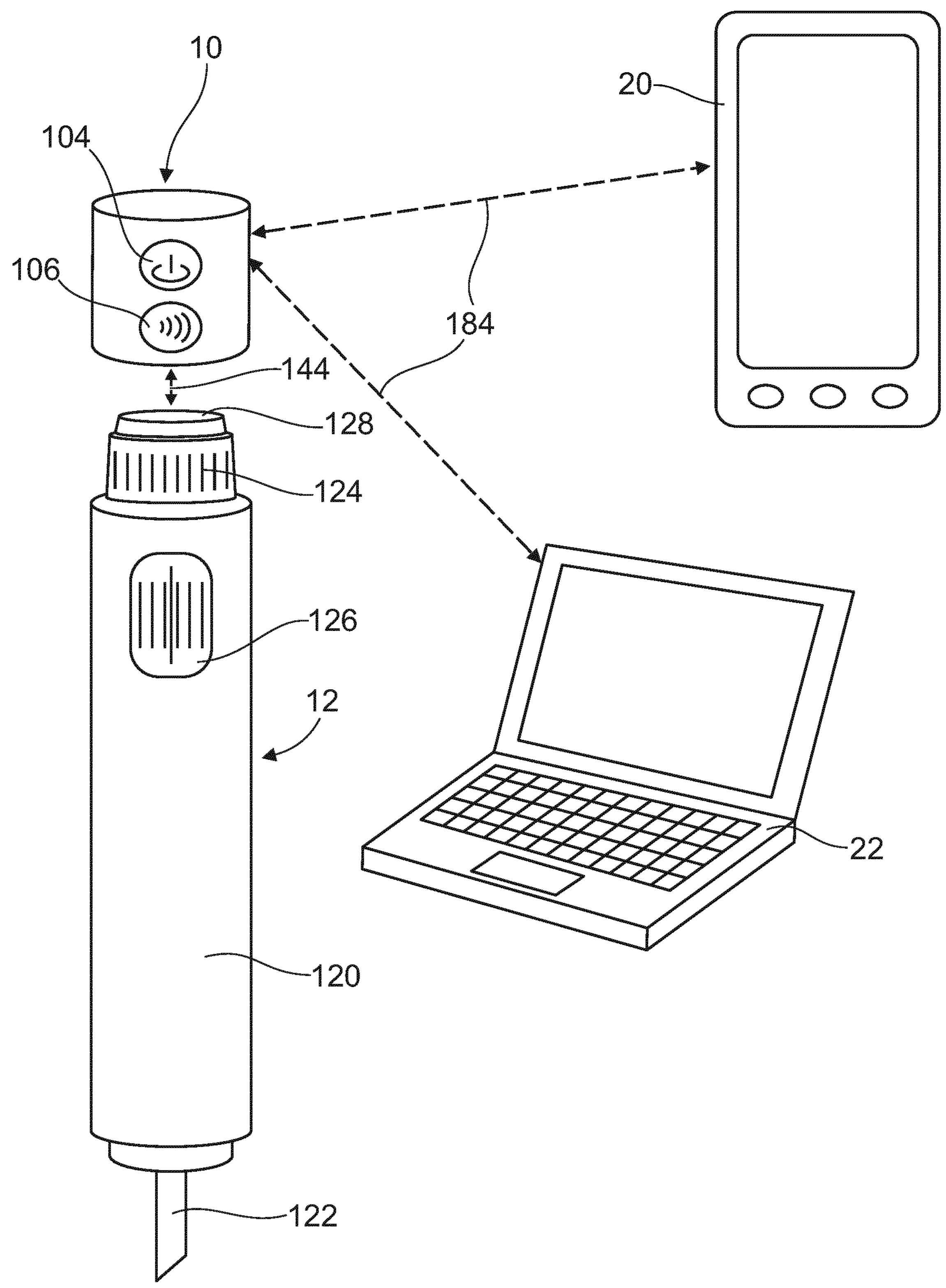
FIG. 1 shows a first embodiment of an accessory for attachment to a drug delivery device.

FIG. 1 shows a drug delivery device 12 in the shape of an insulin injection pen. The device 12 comprises an elongated body 120 having a pen-like shaped form for holding a drug cartridge and a dosage selection and delivery mechanism. At the lower end of the body 120, a syringe 122 for expelling a drug dosage and injecting this dosage in a patient's body is provided. The body 120 comprises at its other, upper end a dial knob 124 for selecting a drug dosage and an injection knob 128 for delivery of a selected dosage. A user of the device 12 selects a dosage by rotating the dial knob 124 around the longitudinal axis of the body 120. The selected dosage is shown on a display 126 integrated in the body 120. After dosage selection, the user may press the injection knob 128 in the direction of the longitudinal axis for expelling the selected dosage via the syringe 122 into a patient's body. The dosage selection and delivery mechanism contained in the body may comprises electronics (not shown) for detecting and for storing and transmitting selected and delivered dosages.

A wireless data communication accessory 10 can be attached to the device 12 by clipping it on the dial knob 124. The accessory 10 houses electronics (not shown) comprising first wireless communication means for establishing a first communication link 184 with an external device such as a smartphone 20 or a laptop computer 22, which may be paired with the wireless communication means, and comprising second wireless communication means and/or wired communication means for establishing a second communication link 144 for exchanging data with a data exchange interface of the device 12. The term "paired" may mean that the accessory 10 and the external devices 20, 22 share some secret data such as cryptographic keys for establishing and/or securing data exchange.

The accessory 10 may comprise a power button 104 for activating and deactivating power supply of the electronics manually. It may further comprise a wireless transmission button 106 provided for initiating a wireless transmission of data from the accessory to the external device 20 and/or 22. The button 106 may be also provided for initiating a pairing process of the accessory's 10 first wireless communication means with an external device 20, 22, for example by pressing the button 106 for a certain time period such as several seconds, thus switching the first wireless communication means in a pairing mode. The first wireless communication means can also be configured to establish automatically a communication link 184 with an already paired external device 20, 22 once the electronics of the accessory 10 is powered and the external device 20, 22 is within a range of maximum communication of the first wireless communication means.

In embodiments, activating the power supply of the electronics of the accessory 10 may be performed automatically, i.e. without manually pressing the button 104, for example by means of an integrated switch of the accessory, which may be activated when the accessory is attached to the device 12 or when a dosage is selected and/or delivered with the device 12. The integrated switch may be for example a mechanical switch or a magnetic switch, which may be activated when the accessory 10 is clipped on the dial knob 124 of the device 12 and/or when the dosage selection and delivery mechanism is used by turning the dial knob 124 and/or pressing the injection knob 128.

The first communication means may be configured for establishing a long-range wireless communication via radio frequency communication such as a Bluetooth® communication link 184 and/or a Wi-Fi™ direct communication link based on the IEEE 802.11 standard (ISO/IEC 8802-11) with the external devices 20, 22 over a distance of at least several centimetres, particularly at least one meter, and more particularly several meters. The maximum distance provided for communication may depend on the power supply requirements of the accessory 10. For example, when the accessory 10 is powered by a one-time usable battery, which should last several months, at least a year or even longer, the maximum distance may be configured by reducing the power requirements of the first communication means to meet the desired battery lifetime. The communication link 184 may be secured due to a pairing process initially made for enabling the communication.

The second wireless communication means may be configured to establish a short-range wireless communication employing electromagnetic induction for data transmission such as a short-range data communication technology based on a RFID (Radio Frequency Identification) standard such as NFC.

Figure 2:
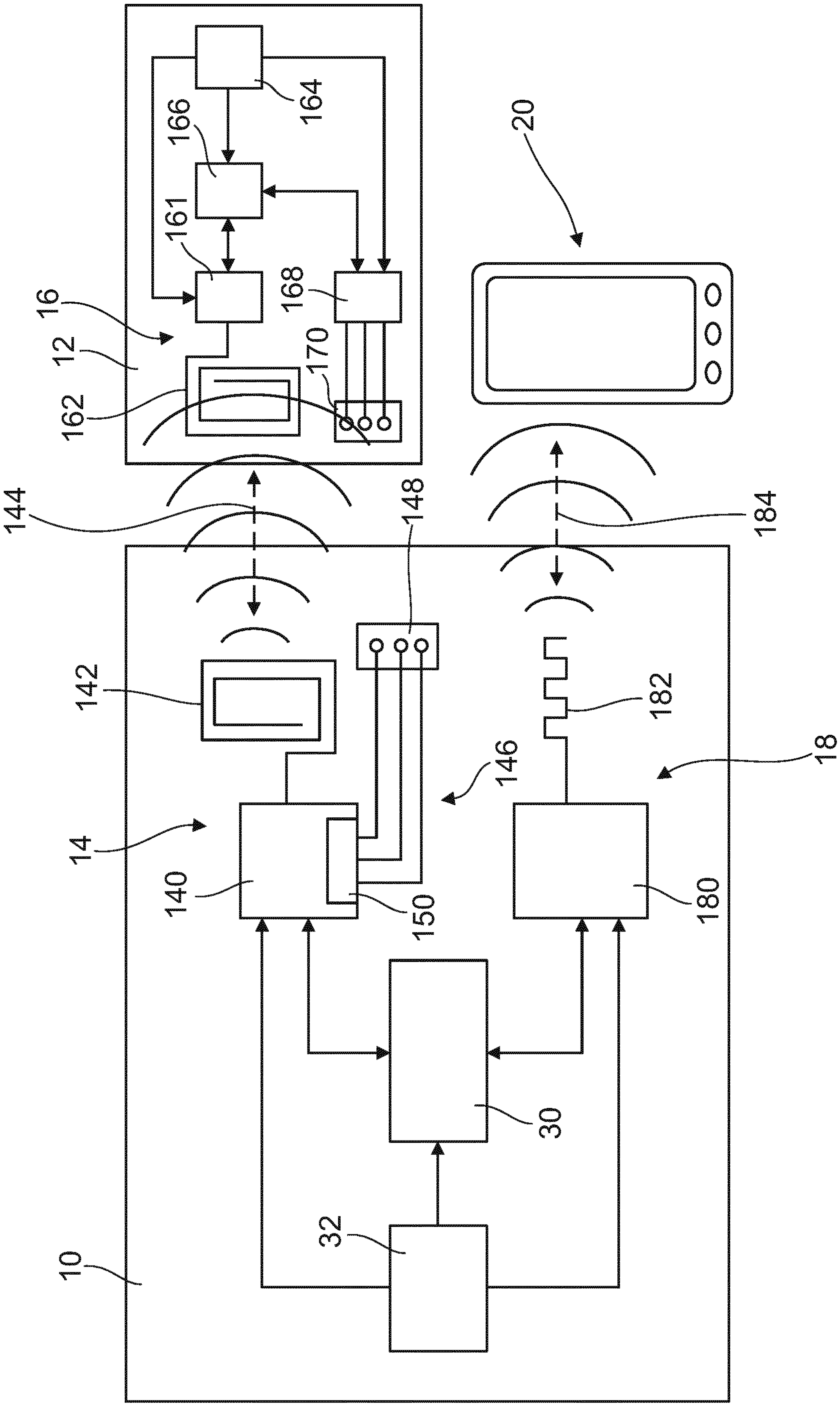
FIG. 2 shows a block diagram of an embodiment of the accessory and of the drug delivery device.

FIG. 2 shows an embodiment of the electronics of the accessory 10 and of the electronics of the drug delivery device 12 as block diagram.

The electronics of the accessory 10 comprises a controller 30, a battery 32, the first wireless communication means 18, and an interface 14 for data exchange with the electronics of the drug delivery device 12, particularly for receiving data related to drug selection and delivery being stored in an internal memory of the drug delivery device 12.

The first wireless communication means 18 comprises a transceiver circuitry 180, for example a Bluetooth® and/or a WiFi™ communication circuitry, and an antenna 182, for example a Bluetooth® and/or a WiFi™ antenna. The transceiver circuitry 180 may be particularly configured to communicate according to the Bluetooth® low energy (BLE) technology.

The interface 14 comprises second wireless communication means, particularly NFC reader circuitry 140 with an NFC loop antenna 142, and/or wired communication means 146 comprising at least one contact 148, particularly a sprung contact, and a serial communication interface circuitry 150 such as an UART/I2C/SPI/1-wire interface circuitry.

The controller 30 is coupled to the interface 14 and the first wireless communication means 18 and may be configured to control operation of these units such that data, which is received from battery 164 powered electronics 160 of the drug delivery device 12 via a short range communication between the second wireless communication means 140, 142 and short-range wireless communication means 16 of the drug delivery device 12, is processed to be transmitted via the first wireless communication means 18 to an external device 20.

The electronics of the drug delivery device 12 comprises a controller 166, a battery 164, and also an interface for data exchange with the electronics of the accessory 10, particularly for transmitting data related to drug selection and delivery being stored in an internal memory of for example the controller 166 of the drug delivery device 12.

The interface of the drug delivery device 12 comprises short range wireless communication means 16, particularly an NFC interface circuitry 161 with an NFC loop antenna 162, and/or wired communication means comprising at least one contact 170, particularly a sprung contact, and a serial communication interface circuitry 168 such as an UART/I2C/SPI/1-wire interface circuitry. The short-range wireless communication means 16, particularly the NFC interface circuitry 161 with the NFC loop antenna 162 may be passive, i.e. inductively powered by the electromagnetic field generated by the NFC loop antenna 142 of the accessory. Thus, for wireless data exchange between the accessory 10 and the drug delivery device 12, power supply from the battery 164 may not be necessarily required or can at least be reduced to a minimum.

The controller 166 is coupled to the interface circuitry 168 and the short range wireless communication means 18 and may be configured to control operation of these units such that data for example related to usage of the drug delivery device 12 being stored in the internal memory can be retrieved and transmitted via the short range wireless communication means 16 and/or the wired communication means comprising the interface circuitry 168 to the accessory 10.

According to embodiments, when a data retrieval request is received either via the interface 16 or the contacts 170 and the interface circuitry 168 from the accessory, the controller 166 may retrieve the requested data from the internal memory and control the interface 16 or circuitry 168 to transmit them via the communication link 144, 184 to the accessory 10.

The electronics of the drug delivery device 12 may be configured to process data retrieval requests from the accessory in an idle, powered off or powered on state. For example, in an idle state, when the controller 166 is switched in a kind of sleep mode if the drug delivery device is not in use, a data retrieval request transmitted from the interface 14 of the accessory may power the wireless interface 16 of the drug delivery device 16, which then may wake-up the controller 166 and power the controller 166 for performing the data retrieval and transmission.

The battery 164 may power the controller 166 and the interface circuitry 168 and also the interface 16 and may be for example a lithium button cell, or a rechargeable lithium-ion battery.

According to embodiments, the electronics of the accessory 10 may also be configured to detect a usage of the drug delivery device 12, particularly when a dosage is selected and/or delivered. The controller 30 may upon a usage detection activate the interface 14 to generate an electromagnetic field with the antenna 142 for powering the short-range wireless communication means 16 and particularly also the controller 166. Thus, the electronics of the drug delivery device 12 may be powered by the electromagnetic field generated by the antenna 142 when the accessory 10 detects a usage of the device 12. More specifically, the amount of electrical power supplied via the electromagnetic field can be made sufficient for covering the entire need of the electronic circuitry in the drug delivery device 12 or, alternatively, to only partly contribute thereto. The latter may be found useful when the power consumption of the short-range communication is expected to have significant impact on the lifetime of an eventual internal power source in the drug delivery device 12. In circumstances, covering the additional need may help to make the lifetime of the internal power source lesser dependent on the incidence and total number of data exchanges and/or may allow using a less powerful internal energy source in the drug delivery device.

In a specific embodiment, the drug delivery device 12 may be implemented without the battery 164 and may comprise only electronics such as the NFC interface circuitry 161 and/or the communication interface circuitry 168 and/or the controller 166. The electronics of the drug delivery device 12 may then be inductively powered by the electromagnetic field generated by the NFC loop antenna 142 of the accessory 10 and/or with power supplied via the at least one contact 170 connected to the contact 148 of the accessory 10.

The embodiment without the battery 164 does not require replacing and/or removing of the empty battery 164, which may make usage and disposal of the drug delivery device 12 more easy for patients. Particularly, disposal of the drug delivery device 12 without a battery may be less critical since it usually less harmful to the environment. Another advantage is the storage of drug delivery devices containing drug cartridges particularly at low temperatures, which is usually critical regarding batteries, which may be harmed by a low storage temperature.

A drug delivery device 12 without the battery 164 requires the accessory 10 for data exchange, particularly for recording and storing selected and expelled dosages. The electronics of a drug delivery device 12 without the battery 164 may be provided to detect and/or store different information drug information, particularly information about the drug contained in the device 12 and/or of selected and expelled drug dosages and information on usage of the device 12. For example, information about the drug contained in the device 12 may be stored in the internal memory of the controller 166 or another storage provided in the drug delivery device 12 such as a flash memory of the short-range wireless communication means 16 and/or of the interface circuitry 168. Further information may be stored such as selected and expelled dosages of the drug and usage information about the device 12 as will be described below.

When the accessory 10 is attached to the drug delivery device 12 without the battery 164, the electronics of device 12 may be powered by the accessory 10, and may for example transmit information on the drug to the accessory 10. Further information stored in the device 12 may be also transmitted, for example the date and time of the first usage and last usage of the device 12, the number of usages, dosage related information such as the date, time, amount of the dosages selected and expelled with the device 12.

The drug information may be stored during production of the device 12, while the usage and dosage related information may be stored while and/or after a usage of the device 12 by a patient. The storing of the latter information requires a power supply from the accessory 10, for example be clipping the accessory 10 to the device 12 and activating the accessory 10.

The powered electronics of the device 12 may cause the controller 166 to execute instructions of a firmware of the device 12, which configure the device 12 to detect selection of a drug dosage and expelling of the selected drug dosage. The detected selected and expelled dosage may then be temporality or permanently stored by the controller 166, particularly in its internal memory, and/or may be transmitted to the accessory 10 immediately after the expelling. The accessory 10 may store the received data in an internal memory and/or transmit it via the communication link 184 to the external device 20.

In addition to the selected and expelled dosages, also time and date and/or usage related information may be stored in the device 12 and/or transmitted to the accessory 10. For example, a counter for the number of usages of the device 12, the time and date of the first and/or last usage of the device 12 may be stored and/or transmitted. The time and date of the first usage and/or last usage may be processed by the accessory 10 to determine the expiration of the drug, for example when the expiration date after the first and/or last usage of the device is exceeded. The accessory 10 can then issue an alert to the patient informing to replace the drug delivery device 12.

The above described storage and/or transmittal of the drug and dosage related information can be implemented also in a drug delivery device 12 containing the battery 164, i.e. a self-powered drug delivery device 12.

In the following, several embodiments are described with drug delivery devices containing batteries. It should be noted that also drug delivery devices without batteries can be applied instead, provided that the accessories attached to the drug delivery devices are embodied to provide a power supply to the electronics of the drug delivery devices as described above with reference to FIG. 2.

Figure 3:
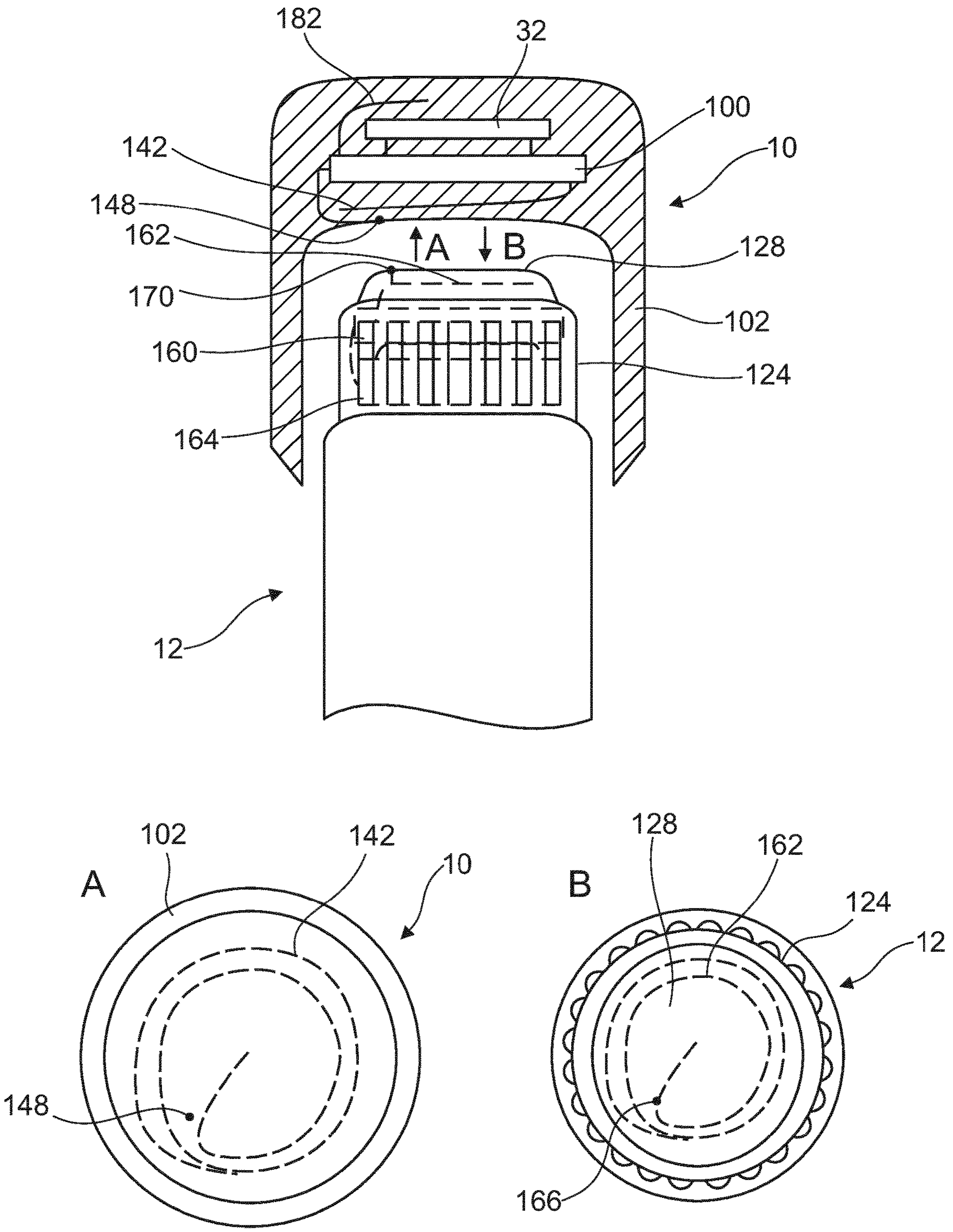
FIG. 3 shows the first embodiment of the accessory in different views.

FIG. 3 shows the accessory 10 and its attachment to the drug delivery device 12 in a partly cross-sectional view and shows a view from the bottom on the accessory 10 and a view from the top on the dial knob 124 of the pen 12.

The accessory 10 comprises a cap-like shaped housing 102, which can be pinned on the dial knob 124 of the insulin injection pen 12. The housing 102 may be made of plastics.

Electronics 100 of the accessory 10, which comprises the controller 30 and the circuitries 140, 180, may be integrated in the housing. The electronics 100 may be for example a printed circuit board on which the elements 30, 140, 180 are soldered and wired, a system on a chip, or an integrated circuit.

The NFC loop antenna 142, the antenna 182, the battery 32 for powering the electronics 100 and optionally one or more contacts 148 may also be integrated in the housing 102. The NFC loop antenna 142 and the optional one or more contacts 148 are located in the interior of the housing 102 such that when the housing is pinned on the dial knob 124 an electromagnetic coupling with an NFC loop antenna 162 integrated in the injection knob 128 may be established for data transmission by induction over a short range of some millimetres or one or more centimetres. If the optional one or more contacts 148 and contacts 170 on top of the injection knob 128 are provided, also a wired connection for a wired data exchange can be established. Contacts 148 and/or 162 may be sprung contacts, and/or conductive pads.

An exemplary position of the NFC loop antenna 142 in the housing's 102 interior can be seen in view A and an exemplary position of the NFC loop antenna 162 in the injection knob 128 can be seen in view B (view directions A and B are shown in the partly cross-sectional view). As can be seen from the views A and B, the position of both antennas 142, 162 in the accessory 10 and the pen 12 is such that an electromagnetic coupling for data transmission may be established once the accessory 10 is pinned on the dial knob 142 of the pen 12 with the antennas 142, 162 facing each other with a distance required for electromagnet induction, or in other words when the planes of extension of the loop antennas are arranged in parallel and close to each other for electromagnet induction.

The antenna 182 for long range communication with an external device may be positioned in the top of the housing particularly so that a wireless communication link 182 with the external device 20 can be established, which is unhindered by the battery 32 and the electronics 100 or the like.

A data exchange between the accessory 10 and the injection pen 12 can be initiated by pinning the accessory 10 on the dial knob 124 and powering the electronics 100 of the accessory 10. The data exchange can be accomplished wireless via NFC or wired via an electric contact between the optional contacts.

For a wireless data exchange, the NFC reader circuitry 140 (FIG. 2) comprised by the electronics 100 generates an electromagnetic field with the NFC loop antenna 142. When the distance between NFC loop antennas 142 and 162 is small enough, the electromagnetic field of the antenna 142 may generate by induction an electric current in the antenna 162, which may supply an NFC transceiver circuitry of the electronics 160 contained in the dial knob 124 of the pen 12 (passive NFC circuitry). The NFC transceiver circuitry of the electronics 160 may then transmit data stored in an internal memory of the pen 12 wirelessly via the antenna 162 to the antenna 142 coupled to the NFC reader circuitry 140 particularly according to an NFC communication protocol. The NFC transceiver circuitry of the electronics 160 may also be an active NFC circuitry, which is powered not by an induction current generated in the antenna 162, but by the battery 164 of the pen 10, which is provided for powering the electronics 160 for recording a dosage selection and injection.

For a wired data exchange, the electronics 100 may first detect whether an electric contact via the contacts 148 and 170 exists, particularly by generating via the interface circuitry 150 (FIG. 2), which may be serial communications interface circuitry, which may particularly comprise an UART interface, an 120 bus interface, a Serial Peripheral Interface, or a 1-wire interface, a signal requesting an acknowledgment of the electronics 160 of the pen 12. If an acknowledgment is received from the electronics 160, the interface circuitry 150 may then initiate a communication via the wired connection between the electronics 100 and 160.

The one or more contacts 170 provided on top of the injection knob may be electrically connected to the antenna 162 as shown in the bottom right drawing of FIG. 3, thus allowing to source an electric current directly via the contact(s) 170 in the antenna 162 such that the wired communication means 146 can read a signal modulation by the electronics 160 of pen 12 on the antenna 162.

Particularly, an NFC reader circuitry 150 may be provided and configured to implement a physical layer of a communications protocol layer being adapted for generating the electric current to be sourced in the contact(s) 170 of the antenna 162 of the pen 12. The sourced electric current may generate a signal corresponding to a wirelessly received signal in the antenna 162, which may be processed by the electronics 160 to generate a reply signal to be transmitted via the antenna 162. This reply signal can then be received by the NFC reader circuitry 150, which is able to read the signal modulation on the antenna 162.

Figure 4:
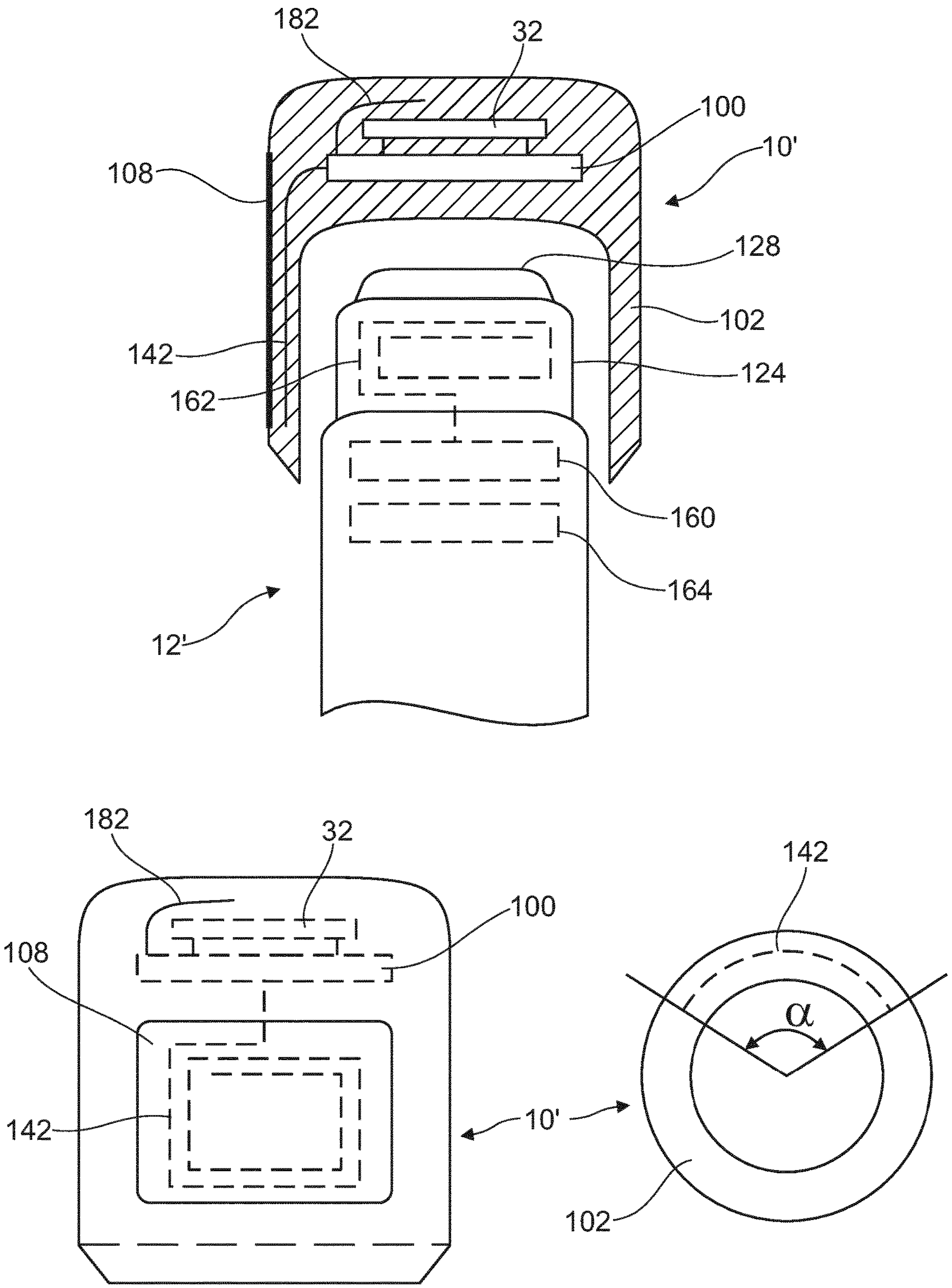
FIG. 4 shows a second embodiment of the accessory in different views.

FIG. 4 shows another embodiment of the accessory 10' and its attachment to the drug delivery device 12' in a partly cross-sectional view and shows a side view of the accessory 10' and a view from the bottom on the accessory 10'.

The accessory 10' also comprises a cap-like shaped housing 102, which can be pinned on the dial knob 124 of the insulin injection pen 12. The housing 102 may be made of plastics.

In this embodiment of the accessory 10' the NFC loop antenna 142 is located at another position in the housing 102, namely in a flange of the housing 102, which overlaps the dial knob 124 of the pen 12', when the accessory 10' is attached to the pen 12'. The position of the NFC loop antenna 142 of the accessory 10' can be also seen in the bottom drawings in FIG. 4, which show a side view of the accessory 10' and view from the bottom on the accessory 10'.

As can be seen in the view from the bottom on the accessory 10', the antenna 142 may extend only over a part of the flange's circumference represented by an angle $\alpha$, which may be between >0° and 360°, particularly as shown in the drawing about 90°. The larger the extension of the antenna, the more power is usually required to generate an electromagnetic field sufficient for data exchange. A smaller the extension of the antenna on the other hand requires a more exact positioning of the antenna 142 and 162 to each other to enable an efficient electromagnetic coupling.

The antenna 162 of the pen 12' may be positioned in wall of the dial knob 124 of the pen 12' in order to make electromagnetic coupling between the antenna 142 of the accessory 10' and the antenna 162 of the pen 12' more efficient, as shown in the top drawing of FIG. 4. Thus, when the accessory 10' is attached to the pen 12' so that the flange of the accessory's housing 102 overlaps the dial knob 142 of the pen 10', the extension planes of both antennas 142, 162 may be arranged coaxially with a distance allowing an electromagnet coupling between the antennas 142, 162 when both antennas are arranged opposite, i.e. when the antenna 142 extending only over a part of the flange's circumference is positioned nearly opposite to the antenna 162.

Figure 5:
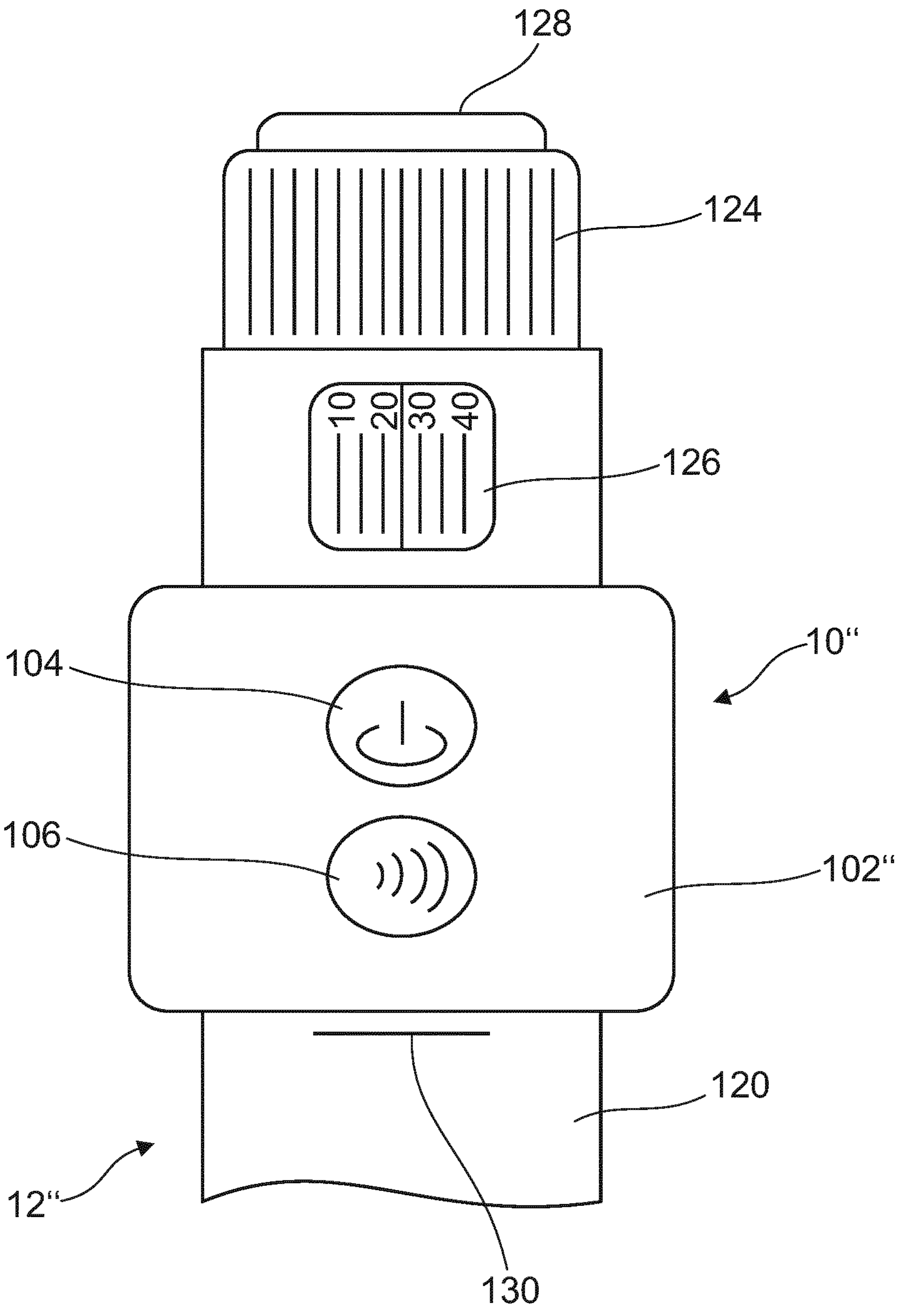
FIGS. 5 to 7 show a third embodiment the accessory in different views.

FIG. 5 shows a yet further embodiment of the accessory 10" and its attachment to the drug delivery device 12". The accessory 10" according to this embodiment comprises a sleeve-like shape housing 102" for pinning on the body 120 of a drug delivery device embodied as an injection pen 12".

Figure 6:
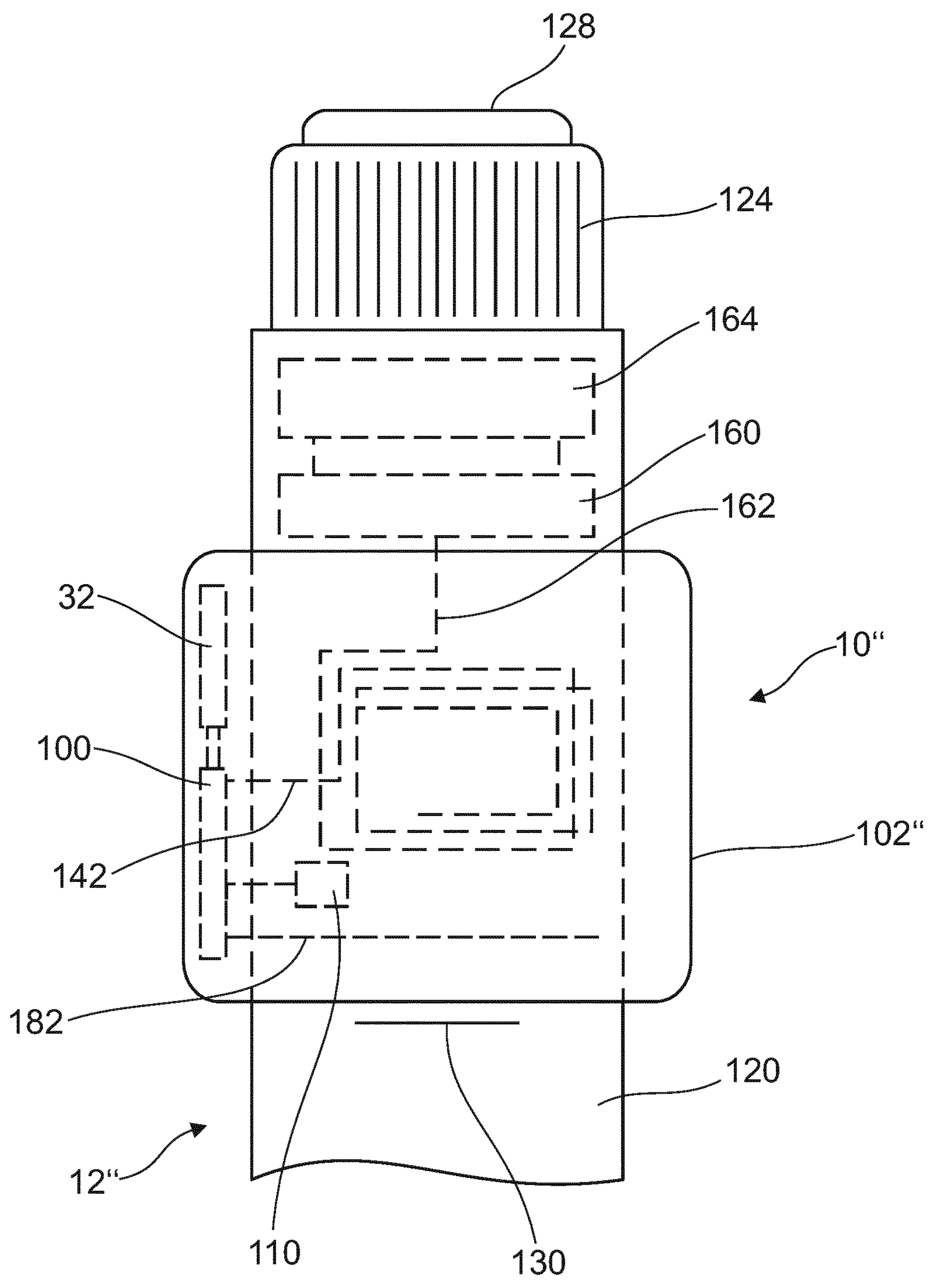

FIG. 6 shows the internal circuitry of the accessory 10" and of the injection pen 12" at least in part. The NFC loop antenna 142 of the accessory 10" is located in the housing 102", particularly below the inner wall of the housing 102". The electronics 100 and the battery 32 are also arranged in the housing 102". Detection means 110 are also provided in the housing 102" for detecting a usage of the pen 12". The detection means 110 may be implemented for example by a magnetic switch configured to detect when a dosage is selected with the dial knob 124 and/or a selected dosage is injected by pressing the injection knob 128. The magnetic switch may for example be triggered by a movement of a metallic part of the pen's 12" internal dosage selection and injection mechanism.

The NFC loop antenna 162 of the pen 12" may be integrated in a wall of the body 120, particularly at a location below the display 126 (FIG. 5). The electronics 160 and the battery 162 may be arranged close to the dial knob 124, for example being integrated in the dosage selection and injection mechanism (not shown) integrated in the body 120 of the pen 12".

For operation, the accessory 10" is slipped over the body 120 of the pen 12", as shown in FIGS. 5 and 6, and may be positioned below the display 126. In such position, the antenna 142 of the accessory 10" may be located over the antenna 162 of the pen 10", or at least close to the antenna 162, so that an efficient electromagnetic coupling between the antennas 142 and 162 may be accomplished. Ideally, both antennas 142 and 162 are coaxially arranged on the axis of the body 120.

Figure 7:
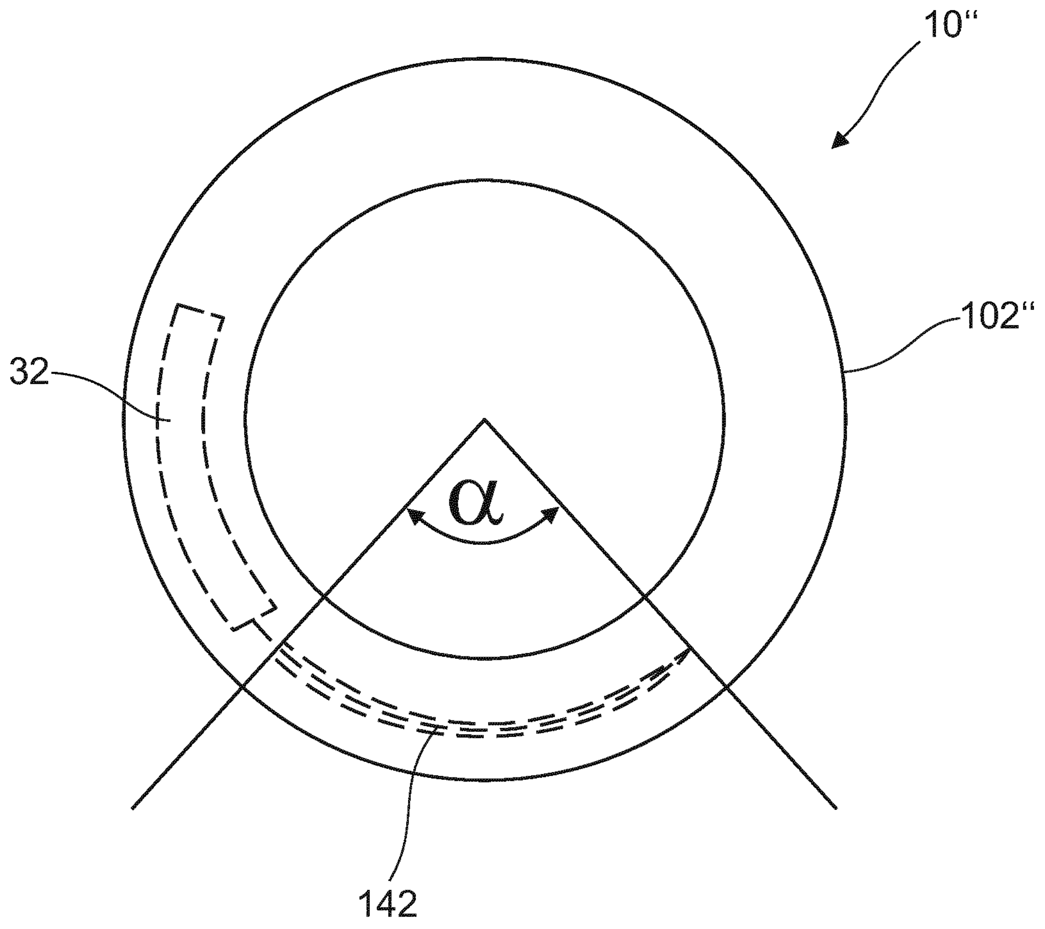

FIG. 7 shows a view on top of the accessory 10" with the arrangement of the battery 32 and the antenna 142 within the housing 102". The extension of the antenna 142 in the circumference of the housing 102" is shown by the angle α, which can be any angle >0° to 360°. In FIG. 7, angle α is about 90° so that a quarter of the cylindrical housing 102" in circumference contains the antenna 142.

A visual marker 130 can be provided on the body 120 of the pen 12" indicating the optimal position of the lower end of the housing 102" of the accessory 10" for obtaining an efficient coupling of both antennas 142, 162. The electronics 100 may also be configured to assist a user in positioning the accessory 10" on the body 120, particularly based on a measurement of the inductive coupling of both antennas 142, 162, and for example signal the optimum positioning audible or visible, for example by means of an LED (Light Emitting Diode) integrated in the power button 104.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®), B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

Abstract

A wireless data communication accessory for a drug delivery device

The invention claimed is:

1. A wireless data communication accessory configured for attachment to a drug delivery device comprising:

an interface for data exchange between the accessory and the drug delivery device;

a wireless communication device configured to communicate with an external device paired with the wireless communication device via wireless communication; and a controller coupled to the interface and the wireless communication device and being configured to control operation of the interface and the wireless communication device such that data received from the drug delivery device via the interface are processed for transmission to the external device via the wireless communication; and a detection device configured to detect a usage of the drug delivery device and to activate a power supply of the accessory upon a detected usage when the accessory being attached to the drug delivery device, wherein the detection device comprises a magnetic switch configured to be triggered by a movement of a part of the drug delivery device during a dosage selection or injection to activate the power supply.

2. The accessory of claim 1, wherein the interface comprises second wireless communication device configured for generating a radio frequency field for powering passive short-range wireless communication device of the drug delivery device and receiving data from the passive short-range wireless communication device via short-range communication.

3. The accessory of claim 2, wherein the second wireless communication device is configured for generating the radio frequency field within a proximity on the order of centimeters and the wireless communication device is configured to communicate with the paired external device within a proximity on the order of meters.

4. The accessory of claim 3, wherein the wireless communication device comprises a Bluetooth® communication circuitry with an antenna configured for Bluetooth® communication and/or the second wireless communication means comprise NFC reader circuitry with an antenna configured for NFC communication.

5. The accessory of claim 1, wherein the interface comprises wired communication device comprising at least one contact for electrically connecting to at least one contact of the drug delivery device when the accessory being attached to the drug delivery device and interface circuitry configured for data exchange via the at least one contact.

6. The accessory of claim 5, wherein the wired communication device is configured to source an electric current via the at least one contact, wherein the electric current is generated to source an electric current in one or more contacts of an antenna of the drug delivery device such that the wired communication device can read a signal modulation by the drug delivery device on the antenna.

7. The accessory of claim 6, wherein the wired communication device comprise a NFC reader circuitry being configured to implement a physical layer of a communications protocol layer being adapted for generating an electric current to be sourced in one or more contacts of an antenna of the drug delivery device such that the wired communication device can read a signal modulation by the drug delivery device on the antenna.

8. The accessory of claim 1, further comprising: a housing being cap-like shaped for pinning on one end of a pen-like shaped drug delivery device.

9. The accessory of claim 1, wherein the detection device is configured to detect a dosage selection on and/or a dosage delivery by the drug delivery device as a usage of the drug delivery device.

* * * * *